United States Patent [19]

Blake et al.

[11] Patent Number: 4,876,504
[45] Date of Patent: Oct. 24, 1989

[54] APPARATUS FOR INVESTIGATING THE CONDITION OF A BACTERIA CONTAINING SUSPENSION THROUGH FREQUENCY PROFILE OF ELECTRICAL ADMITTANCE

[75] Inventors: Barry C. Blake; David J. Clarke, both of Wiltshire, United Kingdom

[73] Assignee: Public Health Laboratory Service Board, England

[21] Appl. No.: 269,173

[22] Filed: Nov. 9, 1988

Related U.S. Application Data

[62] Division of Ser. No. 829,644, filed as PCT GB85/00150 on Apr. 3, 1985, published as WO85/04481 on Oct. 10, 1985, Pat. No. 4,810,963.

[30] Foreign Application Priority Data

Apr. 3, 1984 [GB] United Kingdom ............... 8408529

[51] Int. Cl.⁴ ................. G01N 27/74; G01N 27/02; G01R 27/22; A61B 5/05
[52] U.S. Cl. ................................... 324/204; 128/635; 324/57 R; 324/71.1; 324/263; 324/445
[58] Field of Search ............... 324/71.1, 71.4, 204, 324/234, 236, 239, 445, 263, 57 R, 57 SS; 204/403; 422/68; 128/632, 635, 734

[56] References Cited

U.S. PATENT DOCUMENTS

| | | | |
|---|---|---|---|
| 2,709,785 | 5/1955 | Fielden | 324/204 X |
| 2,795,759 | 6/1957 | Rezek | 324/445 |
| 3,007,107 | 10/1961 | Gondouin | 324/359 |
| 3,316,896 | 5/1967 | Thomasset | 324/71.4 X |
| 3,433,057 | 3/1969 | Halsey | 324/204 X |
| 3,477,018 | 11/1969 | Richardson et al. | 324/236 X |
| 3,719,882 | 3/1973 | Pincus | 324/236 X |
| 3,723,862 | 3/1973 | Wentzel et al. | 324/236 |
| 4,282,487 | 8/1981 | Warren et al. | 324/204 X |
| 4,580,096 | 4/1986 | Liedholz | 324/204 |
| 4,785,239 | 11/1988 | Brunsch et al. | 324/204 |

FOREIGN PATENT DOCUMENTS

480967 12/1975 U.S.S.R. .............................. 324/445

Primary Examiner—Gerard R. Strecker
Attorney, Agent, or Firm—Lowe, Price, LeBlanc, Becker & Shur

[57] ABSTRACT

A method of investigating the condition of biological particles, in particular the fraction of viable cells in a bacteria population involves applying a voltage and monitoring the voltage induced by magnetic induction in a detector coil. The applied voltage is of a variable frequency alternating voltage and is preferably induced in the medium through a drive coil.

7 Claims, 9 Drawing Sheets

FIG.3a) KPI 10mM/5-500KHZ/10V SIG (SCAN 14)

4,876,504

APPARATUS FOR INVESTIGATING THE CONDITION OF A BACTERIA CONTAINING SUSPENSION THROUGH FREQUENCY PROFILE OF ELECTRICAL ADMITTANCE

This is a divisional application of our earlier application Ser. No. 829,644 filed as PCT GB85/00150 on Apr. 3, 1985, published as WO85/04481 on Oct. 10, 1985, now Pat. No. 4,810,963.

FIELD OF THE INVENTION

This invention relates to a method and apparatus for investigating the condition of biological particles, such as bacteria, in a medium. In one example the invention is concerned with establishing what fraction of the bacteria are viable.

BACKGROUND OF THE PRIOR ART

Work has previously been carried out in investigating the electrical impedance of suspensions of certain bacteria. It has been established that the impedance consists primarily of resistive and capacitive components, though the measured conductivity and relative permittivity are not constant but functions of frequency. In a plot of relative permittivity against frequency, it is possible to identify alpha and beta dispersions which are believe to relate to the respective contributions of different membrance layers in the bacterium. Each membrane layer is believed to function, as a resistance/capacitance network with the relative contribution of the various layers changing with frequency. The alpha dispersion has been associated with the outer membrane layers and the beta dispersion with the innermost layers.

The traditional approach to the measurement of impedance of bacterium suspensions involves manual bridge techniques. These are time consuming and require very careful attention to balancing and calibration. The procedures do not lend themselves to use in a bioreactor on a commercial scale where real time, continuous monitoring is required.

A number of commercially available impedance analysers have been suggested for use in investigating dieletric dispersion in suspensions. The difficulty here is that the impedance analysers are constructed and organized to operate on networks of unknown but constant resistance, capacitance and inductance. Very careful further analysis is required, bearing in mind that the conductivity and relative permittivity of the suspension are known to be functions of frequency, before the output of a commercially available impedance analyser can provide useful information in this context.

SUMMARY OF THE INVENTION

It is an object of one aspect of this invention to provide improved method and apparatus for investigating the concentration of biological particles which is capable of distinguishing, for example, between viable and non-viable bacteria.

Accordingly, the present invention, in one aspect, consists of a method of investigating the condition of biological particles in a medium, comprising the steps of applying an alternating voltage of varying frequency across a body of medium; monitoring the voltage induced in a detector coil adjacent the medium and deriving a frequency profile of composite medium and particle admittance.

In another aspect, the present invention consists in apparatus for investigating the condition of biological particles in a medium, comprising a chamber filled in use with the medium; electrode means for applying a voltage across medium in the chamber; voltage generator means for generating an alternating voltage of selected frequency at said electrode means; coil means so disposed that the voltage induced therein is indicative of the magnetic field associated with current flow in the medium and processor means for compiling a profile of measured voltage in the coil means against frequency of voltage applied to the electrode means.

Advantageously, the processor comprises storage means for storing the profiles.

Suitably the chamber comprises a conduit through which medium may flow continuously and, preferably, the conduit is cylindrical and the coil means comprises a helical coil having its axis orthogonal to the axis of the cylinder.

In another form, the present invention consists in apparatus for investigating the condition of biological particles in a medium, comprising a chamber filled in use with the medium; drive coil means for inducing a voltage in the medium; voltage generator means for applying an alternating voltage of variable frequency to said drive coil means, detector coil means so disposed that the voltage induced therein is indicative of the magnetic field associated with current flow in the medium and processor means for compiling a profile of measured voltage in the detector coil means against frequency of voltage applied to the drive coil means.

Advantageously, said voltage generated means is adapted to vary the magnitude of the generated alternating voltage so as to maintain a constant magnitude current in the drive coil at varying frequencies.

By deriving an impedance/frequency profile for the same suspension at different times, it will be possible through comparison to detect a shift in weighting of the alpha and beta dispersions identifiable with the change in the proportion of viable bacteria. In the example of a bacterium it is necessary to distinguish between viable bacterium and "ghosts" comprising ruptured cell walls from which the cytoplasm has been lost. It is believed that the "ghost" will contribute to the alpha dispersion which is associated with the outer cell layers but will make no contribution to the beta dispersion. A relative increase in the weighting of the alpha dispersion can thus be interpreted as a decrease in the number of viable cells.

In another aspect, the present invention consists in a method of investigating the concentration of biological particles in a medium comprising the steps of amplifying a voltage induced by alternating current flow through a body of the medium; applying said voltage to the medium to excite resonance and determining the frequency of resonance.

In yet a further aspect, the present invention consists in apparatus for investigating the concentration of biological particles in a medium, comprising a chamber filled in use with the medium; electrode means for applying a voltage across medium in the chamber; coil means so disposed that the voltage induced therein is indicative of the magnetic field associated with current flow through the medium; amplifier means for presenting said induced voltage to the electrode means in a manner to excite resonance and means for measuring the resonant frequency.

BRIEF DESCRIPTION OF THE DRAWING

The invention will now be described by way of example with reference to the accompanying drawings in which.

Figure 4:
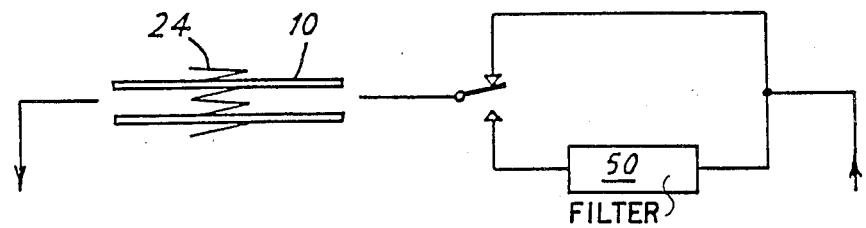
Figure 3B:
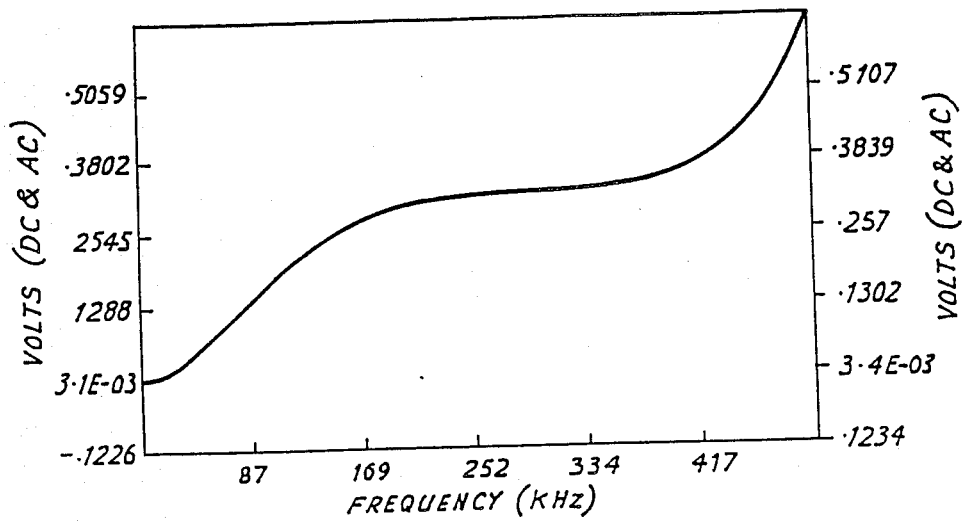
Figure 3B:
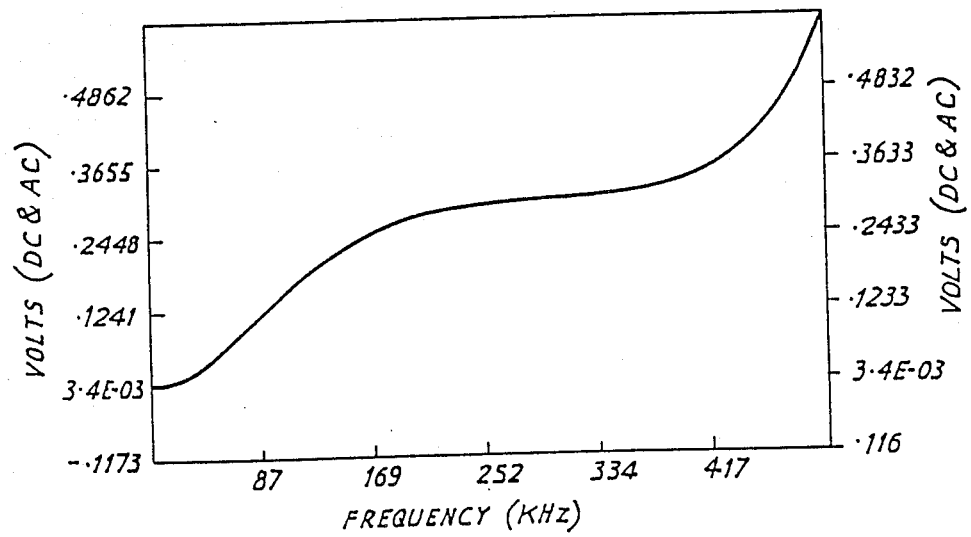
Figure 3C:
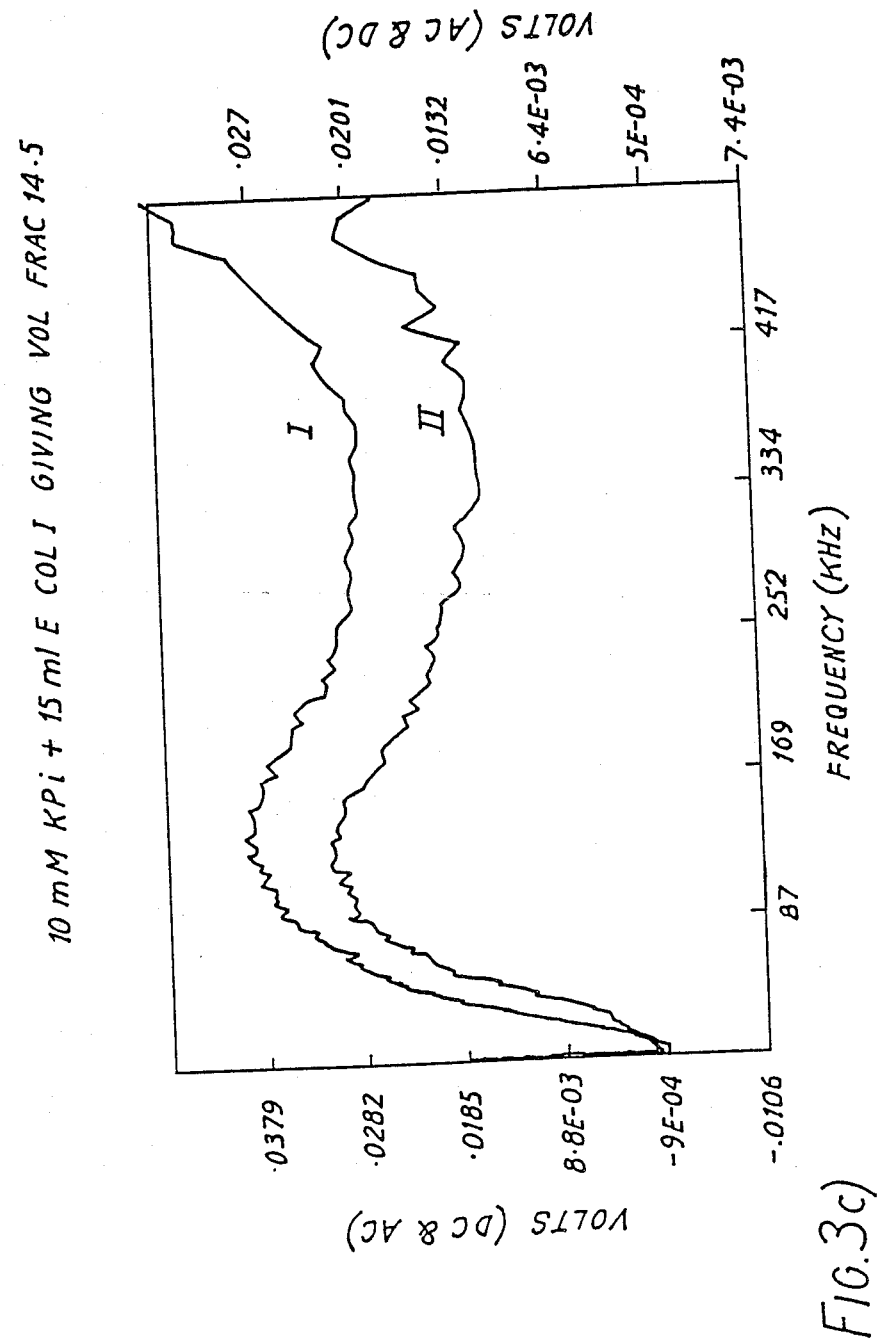
Figure 5:
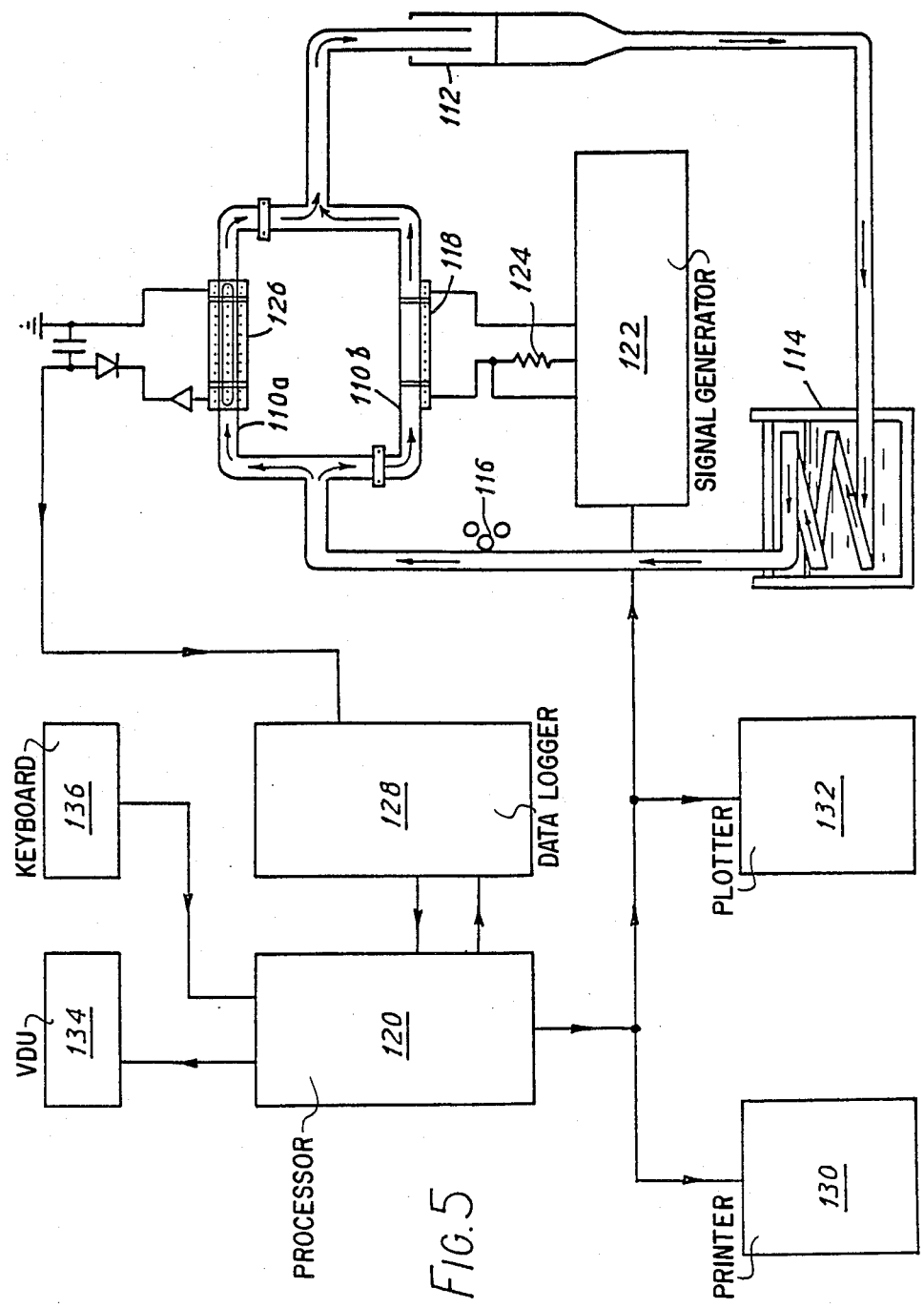
Figure 6:
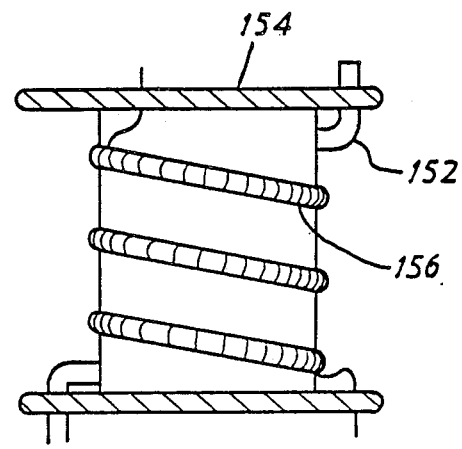
Figure 8:
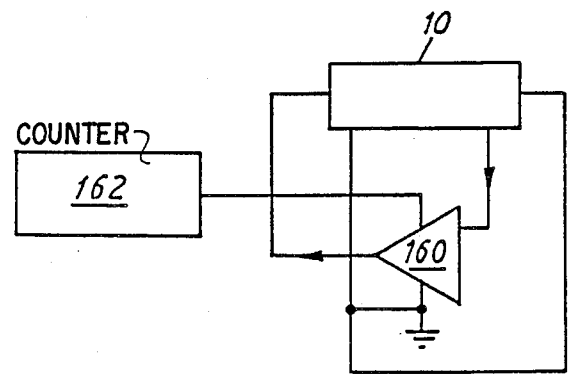

FIGS. (3a), (b) and (c) are illustrative frequency plots;

FIG. 4 is a block diagram of alternative apparatus according to this invention;

FIG. 5 is a partly diagrammatic view of apparatus according to another embodiment of the invention;

FIG. 6 illustrates a variation of test cell for use in the present invention; and FIGS. (7a) (b) and (c) are illustrative frequency plots; and FIG. 8 is a diagram of yet further apparatus according to this invention.

DESCRIPTION OF THE PREFERRED EMBODIMENT

Figure 1:
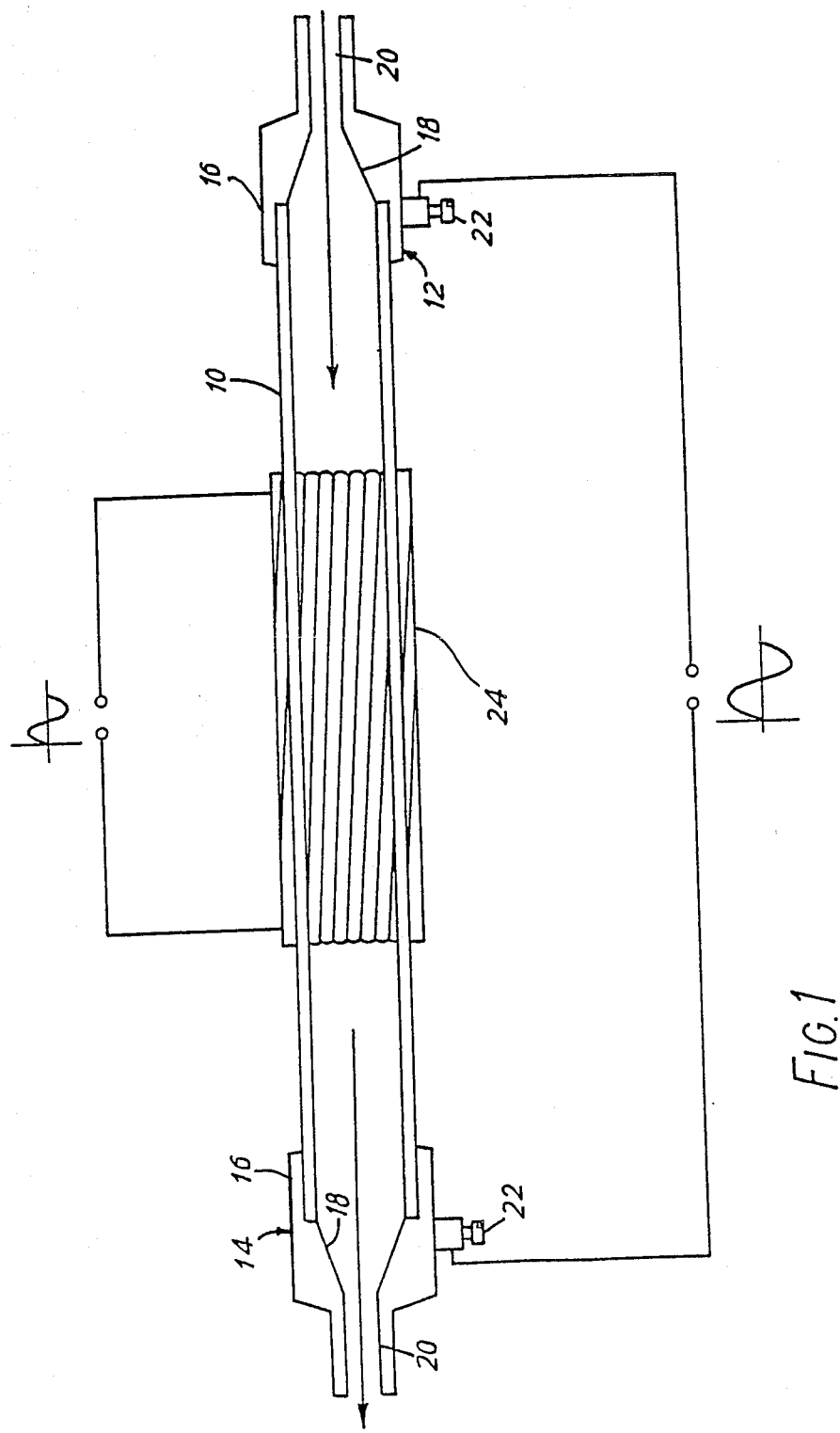
FIG. 1 illustrates somewhat diagrammatically a test cell for use in this invention.

Referring to FIG. 1, a test cell according to this invention is shown comprising a silica or pyrex glass tube 10 having electrodes 12 and 14 bonded to each end thereof. The electrodes are identical and comprise a cup portion 16 which surrounds the end of the glass tube, the interior surface of the cup portion being formed with a rebate to ensure a smooth composite surface. The electrode has an inner conical surface 18 which opens to an aperture 20 and serves as a sample fluid inlet/outlet. An electrode connector 22 of conventional form is provided on each electrode. Between the electrodes, the tube 10 carries on its outer surface a tightly wound helical coil 24. The coil 24 is arranged on suitable formers (not shown) with the axis of the coil orthogonal to the axis of the tube.

It will be understood that with a conductive medium in the glass tube, the application of an alternating voltage across electrodes 12 and 14 will result in the passage of a current in the medium, this in turn creating an oscillating magnetic field inducing a voltage across the coil, the turns of which cut the field.

Figure 2:
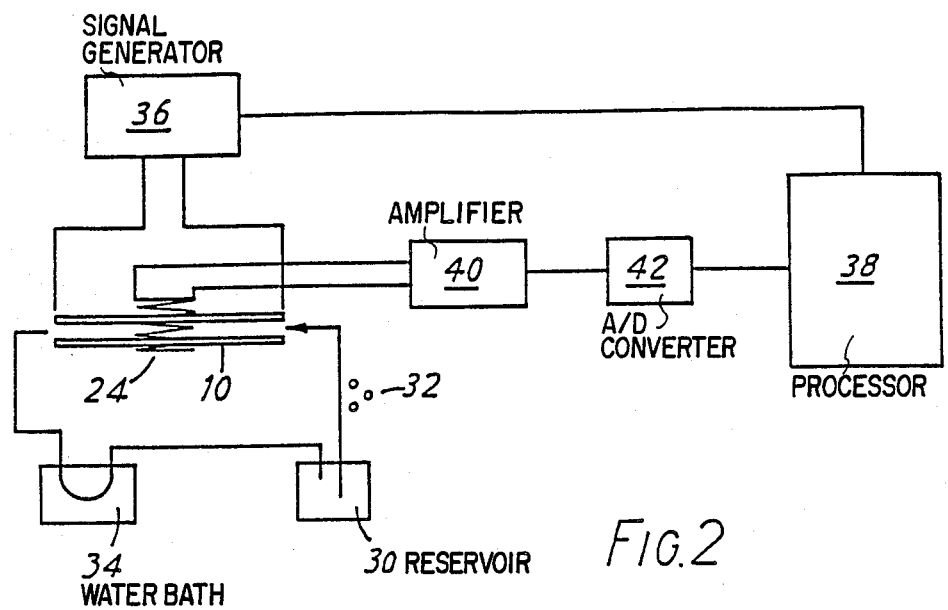
FIG. 2 is a block diagram of apparatus according to this invention including the test cell of FIG. 1.

With reference to FIG. 2, a system will now be described for deriving information from this induced voltage and its variation with frequency.

The test cell which is shown in FIG. 1 is connected with a medium reservoir 30, a peristaltic pump 32 and a water bath 34 so as to establish a uniform flow of a sample fluid through the cell at a constant temperature. In an alternative arrangement, a sample of fluid may be diverted continuously from a chamber or feed line of a bioreactor and passed through the temperature bath to the cell. A signal generator 36 is connected with the electrodes 12 and 14 to apply across those electrodes a sinusoidal voltage of fixed amplitude and of a selected frequency. Processor 38 is connected with the signal generator 36 to cause the signal generator to sweep through a frequency range. The processor 38 enables preselection of the signal amplitude, the number of frequency sample points, the delay between samples, the number of repeat samples of any one frequency and the frequency range of interest.

The alternating voltage induced in the coil 24 is passed to an amplifier 40 having a high gain at low frequencies. The response of the amplifier is selected to compensate at low frequencies for the frequency variation of induced voltage according to Faraday's law. At higher frequencies, the induced voltage is sufficiently large not to require amplification. The output of the amplifier 40 is passed through analogue-to-digital converter 42 to the processor 38.

Through suitable sampling, the processor compiles a profile of induced voltage against frequency, including—say—300 data values in a particular frequency band. An example of such a profile for an *E Coli* suspension is shown in FIG. (3a). A qualitative comparison reveals that there has been a shift in the relative weights of the alpha and beta dispersions which is indicative of a change in the proportion of viable bacteria.

In order to enable quantitative evaluation, a profile can be compiled for medium from which bacteria have been separated. This may be achieved, for example, using the apparatus shown in FIG. 4 where the flow of sample may be taken either directly to the test cell or through a filter 50 arranged to separate bacterium or other biological particles. The numerical profile generated for medium devoid of bacteria is stored in the processor and used as a baseline for evaluation of subsequent profiles. An example of a frequency plot for medium only is shown at FIG. (3b).

The result of subtracting the plot of FIG. (3b) (medium only) from the plot of FIG. (3a) (medium +*E Coli*) is shown in plot I of FIG. (3c). The portion between the maximum at approximately 100kHz and the minimum at approximately 350kHz can be interpreted as the alpha dispersion with the difference in voltage terms between these two points being indicative of the strength of the alpha dispersion. As mentioned above, the alpha dispersion is associated with the outer cell membranes. Plot II corresponds to a suspension in which a proportion of the bacteria have died. It can be seen qualitatively that the strength of the alpha dispersion has increased. For a quantitative analysis a comparison of the relative weightings of the alpha and beta dispersions is made, the beta dispersion being found at higher frequencies—typically 50 MHz.

Referring now to FIG. 5, there is shown a further embodiment of this invention. A recirculating pathway for medium is established through parallel paths 110a, 110b; a reservoir 112; a temperature controlled bath 114 and peristaltic pump 116. Parallel limb 110b carries on its outer surface a coil 118 wound with its axis orthogonal to the pathway and parallel to the plane of the paper. Under control from a processor 120 a signal generator 122 applies an alternating voltage across the coil 118 at a selected and variable frequency. The connection between the signal generator and the coil includes a series precision resistor 124 and a tap is taken from the resistor to enable current sensing within the signal generator.

It is important that, whatever the frequency, a constant drive current should flow in the coil 118 and there is therefore contained within the signal generator 122 a comparator which produces an error signal if the sensed current (as represented by the voltage across the precision resistor 124) departs from a preset current level. If the sensed current drops below the desired current, the amplitude of the voltage applied by the signal generator is increased. To enable this condition of constant current to be met over a useful range of frequencies, the signal generator includes a power amplifier.

The oscillating magnetic field created by the coil 118 will induce a voltage in the medium causing current to flow along the length of the pathway. This current will tend to circulate round parallel pathways 110a and 110b. To detect this current, a detector coil 126 is disposed on the outside of limb 110a. This coil is similar to coil 118 but has its axis orthogonal to the plane of the paper. The voltage induced in the detector coil 126 is amplified, rectified and passed to data logger 128. The processor 120 is further connected in conventional manner with a printer 130, a plotter 132, a VDU 134 and a keyboard 136.

Figure 7A:
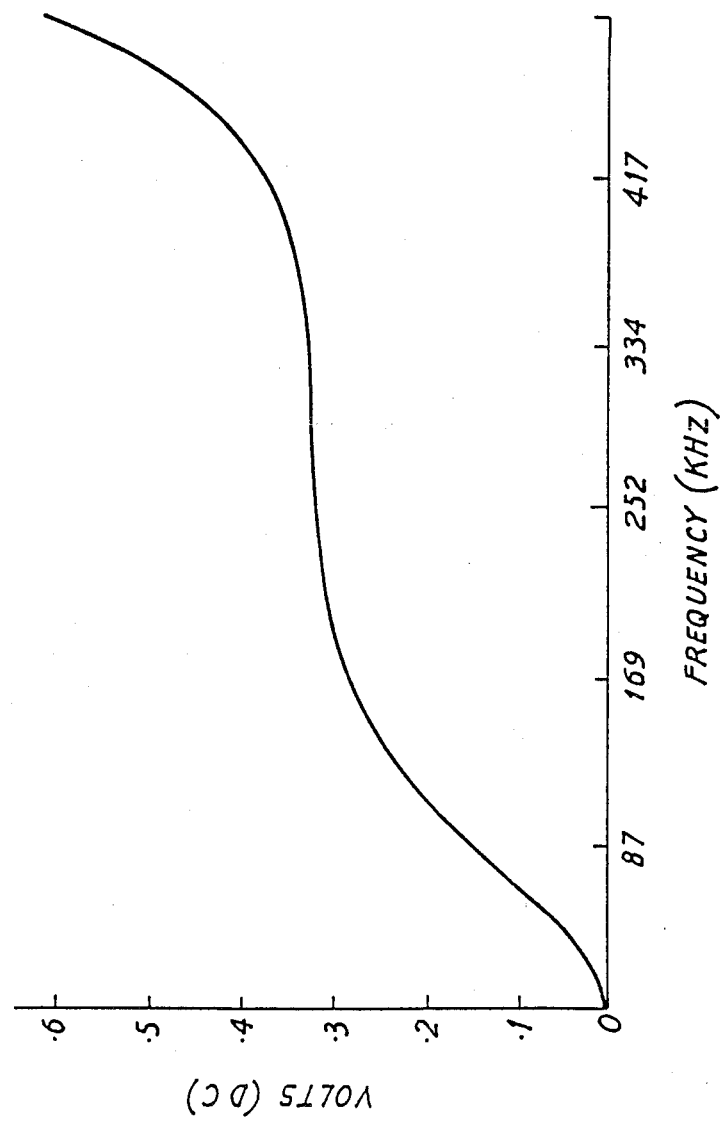
Figure 7B:
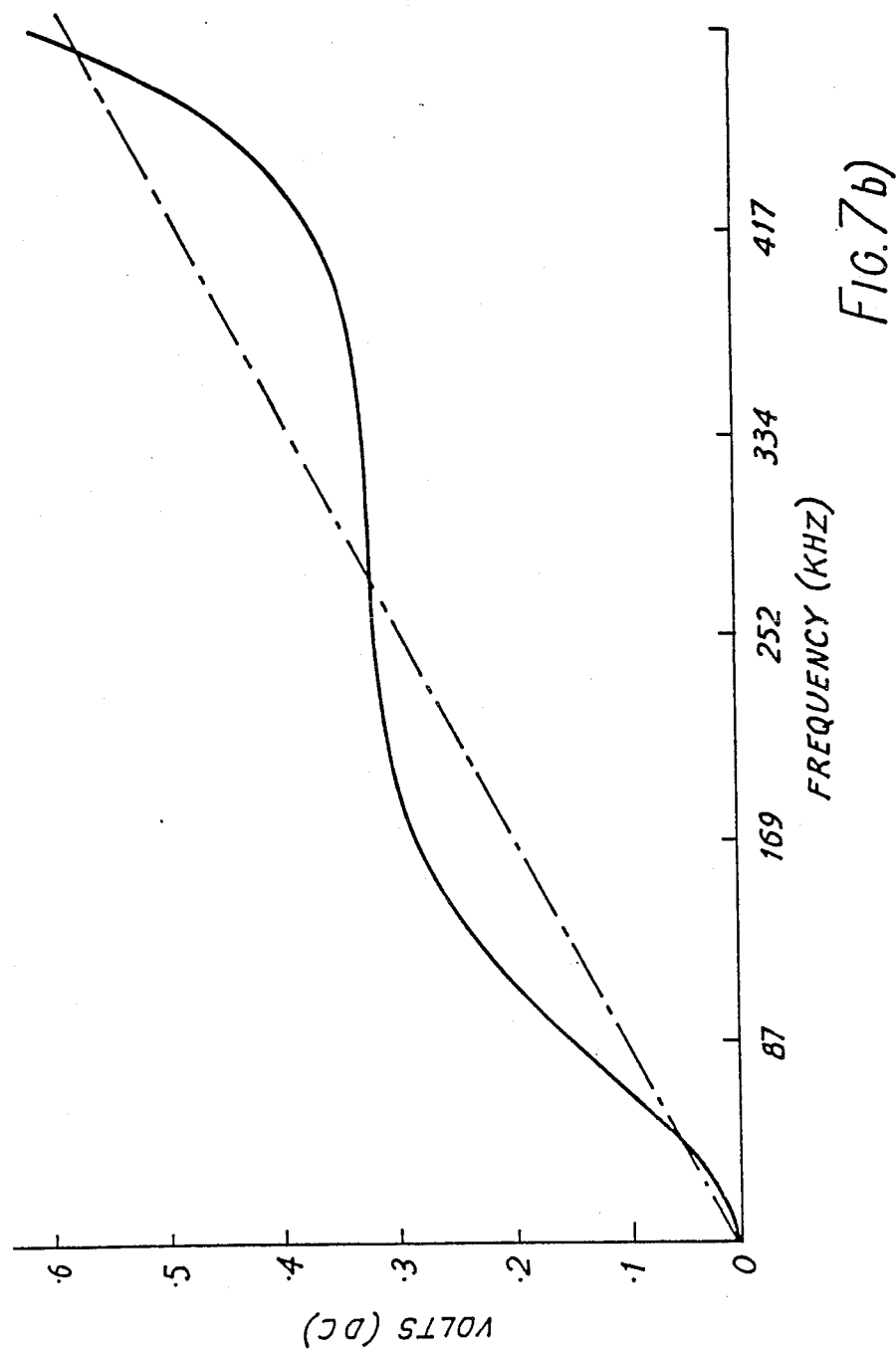
Figure 7C:
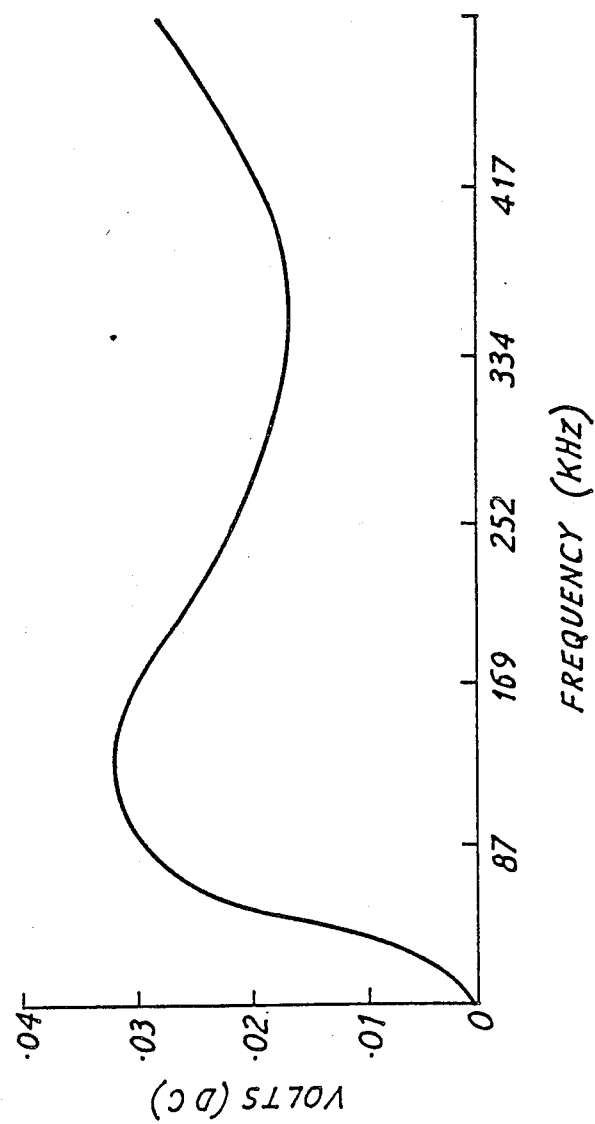

In operation, the processor causes the frequency of the voltage applied to the drive coil 118 to sweep through a desired frequency band. As described, it is ensured that the current in the drive coil is sensibly constant. Throughout the frequency sweep, the voltage in the detector coil 126 is sampled. In one example, a suspension of *E Coli* of volume 14.5% in a nutrient medium was passed through the parallel limbs 110a, 110b. The frequency of the applied voltage was swept from 500 Hz to 500 kHz. A profile of detector coil voltage against frequency was produced and is shown at FIG. 7a. The frequency sweep was repeated with medium from which bacteria had been removed by filtration and profile for the medium alone is shown at FIG. 7b. In this Figure, the dot dash line represents a calibration line achieved with an ohmic liquid in the flow path. By subtracting the profiles of FIGS. (7a) and (7b), the profile of FIG. FIG. ) is produced which contains the desired information concerning the bacteria alone. In this profile of FIG. (7c), the alpha dispersion is clearly visible. With repeated measurements during the life of a population of bacteria, changes in the weighting of the alpha dispersion can be measured as described above.

In another modification a test cell suitable for use at very high frequencies is shown in FIG. 6 where the glass tube of FIG. 1 has been replaced by a flexible PTFE tube 152 wound about a non-conductive former 154. The coil 154 is open wound about the PTFE tube 152. In another respect this modified test cell is used in a manner analogous to that described in FIG. 1.

In yet a further alternative arrangement according to the invention, the test cell is incorporated into a closed oscillatory circuit such that the cell contents have the dominant role in determining the resonant frequency of the system. This is achieved by using the flux linkage between the conductive cell contents and the feed coil as the positive feedback path between the input and output of a high gain amplifier. The amplifier response can be wideband or frequency controlled depending upon the application; but in either case may be so designed as to have an amplitude dependent gain system thereby allowing the system to monitor fluids where a reactive component is the primary variable or the measured range of conductivities is too low to maintain oscillation. Referring to FIG. 8, the detector coil is connected to the high impedance input of an amplifier 160, and, as required, the drive coil or electrodes are supplied from the low impedance output of the amplifier. In practice, one end of each coil or one of the electrodes are connected to ground. An output is taken from an intermediate stage of the amplifier to a high resolution counter 162, measuring the period of resonant oscillation.

It is found that the frequency of oscillation varies with the population of viable bacterium suspended in the medium. A decrease in the number of viable bacteria is identified by a reduction of oscillation frequency. It is believed that this behaviour can be explained by the release of additional electrolyte into the medium which occurs on rupture of a cell wall. A decrease in the number of viable cells therefore results in a reduction of the dielectric component but an increase in electrolytic conduction. The time constant therefore increases and the frequency of resonance drops.

It should be understood that this invention has been described by way of examples only and a variety of modifications are possible without departing from the scope of the invention. Thus whilst reference has been made throughout to test cells through which medium passes continuously, apparatus according to this invention can function with a stationary volume of medium in a test cell or indeed with electrodes dipped in a body of sample in the manner of a probe.

In terms of analysis, it has been found that with one particular bacterium—*E Coli*—investigation of the strength of the alpha dispersion reveals useful information concerning viability. Under other circumstances and with different micro-organisms, alternative forms of analysis will be appropriate.

The invention in its various forms has particular application in determining the proportion of bacteria in a population which are viable, but may have other applications in investigating the concentration of biological particles in a medium which may be a suspension, slurry or colloid. In parts of the described methods, apparatus according to this invention is employed to determine the impedance of medium from which biological matter has been separated, in order to provide reference levels. This usage may be extended to cases where the impedance (or conductivity) measurement of the medium is the primary concern.

We claim:

1. Apparatus for investigating the condition of a suspension of bacteria in a medium, comprising:
   a chamber comprising a conduit filled with the medium in use;
   a pair of electrodes positioned to contact said medium contained within the chamber;
   means for producing a controlled continuous flow of said medium through said conduit between said electrodes;
   voltage generator means electrically connected with said electrodes and serving to generate an alternating voltage of selected frequency across said electrodes, thereby causing an alternating current to flow in said medium therebetween;
   coil means disposed so that a time varying voltage is induced therein by a time-varying magnetic field associated with said alternating current flow in the medium;
   means for measuring said induced voltage; and
   processor means, including means for controlling said voltage generator means to generate said alternating voltage at a plurality of frequencies and for also controlling said measuring means to provide an output corresponding to said induced voltage at said frequencies for generating a profile therefrom of measured induced voltage in the coil means as a plot thereof against a plurality of different selected frequencies of the alternating voltage applied to the electrode, said profile being indicative of a condition of the bacteria suspended in said medium.

2. Apparatus according to claim 1, wherein:
   the processor means comprises storage means for storing at least one of said profiles.

3. Apparatus according to claim 1, wherein:

the conduit is cylindrical and the coil means comprises a helical coil having its axis orthogonal to the axis of the conduit, said electrodes being separated along said conduit.

4. Apparatus according to claim 1, wherein the electrode means comprises:
the two electrodes are disposed to be one at each end of the conduit, both electrodes being apertured to permit flow of said medium therethrough.

5. Apparatus for investigating a condition of a suspension of bacteria in a medium, comprising:
a chamber filled in use with a controlled flow of the medium in a first direction;
drive coil means positioned adjacent the chamber with an axis of the drive coil means oriented to be orthogonal to said first direction;
variable frequency, constant amplitude current drive means for causing an alternating current to flow at constant amplitude through the drive coil means, such that a time varying magnetic field associated with the drive coil means causes a corresponding alternating current to flow in the medium;
detector coil means so disposed adjacent the chamber that a voltage is induced therein by a time varying magnetic filed associated with said alternating current flow in the medium, an axis of said detector coil means being oriented to be orthogonal to said first direction and to said drive coil means;
means for measuring the voltage induced in the detector coil means; and
processor means, including means for controlling the variable frequency current drive means to generate said variable frequency constant amplitude current and also for controlling said measured induced voltage measuring means to provide an output corresponding to said induced voltage at said frequencies for generating therefrom a profile of measured induced voltage as a plot thereof against a plurality of different selected frequencies of said variable frequency constant amplitude current, said profile being indicative of a condition of the bacteria suspended in said medium.

6. Apparatus according to claim 5, wherein:
the constant amplitude current drive means comprises a voltage generator means for applying an alternating voltage of variable frequency to said drive coil means, current sensing means for sensing a current flow in the drive coil means, and feedback means for varying the amplitude of said applied alternating voltage in dependence upon said sensed current flowing in the drive coil means.

7. Apparatus according to claim 5, wherein:
said processor comprises storage means for storing profiles and comparator means for comparing profiles.

* * * * *